United States Patent [19]

Uematsu et al.

[11] 4,337,357
[45] Jun. 29, 1982

[54] HERBICIDAL DITHIO-BIS(HALOACETANILIDES)

[75] Inventors: Tamon Uematsu, Toyonaka; Shunichi Hashimoto, Takarazuka; Hiromichi Oshio, Minoo, all of Japan

[73] Assignee: Sumitomo Chemical Company, Limited, Osaka, Japan

[21] Appl. No.: 200,339

[22] Filed: Oct. 24, 1980

Related U.S. Application Data

[62] Division of Ser. No. 28,801, Apr. 10, 1979, Pat. No. 4,268,301.

[30] Foreign Application Priority Data

Apr. 17, 1978 [JP] Japan .................................. 53-45766
Oct. 13, 1978 [JP] Japan .................................. 53-126378

[51] Int. Cl.³ ........................ A01N 9/12; C07C 103/38
[52] U.S. Cl. .................................. 564/154; 564/143; 71/98
[58] Field of Search .............................. 564/143, 154

[56] References Cited

U.S. PATENT DOCUMENTS

| | | | |
|---|---|---|---|
| 2,470,945 | 5/1948 | Paul | 564/154 X |
| 3,573,320 | 3/1971 | Jansen et al. | 564/154 X |
| 3,998,883 | 12/1976 | Nakanishi et al. | 564/143 X |
| 4,190,663 | 2/1980 | Böshagen et al. | 564/154 X |

FOREIGN PATENT DOCUMENTS 1061103  4/1954  France .............................. 564/154

OTHER PUBLICATIONS

Borgna et al., CA 81:34416c (1974).

*Primary Examiner*—Thomas A. Waltz
*Attorney, Agent, or Firm*—Wenderoth, Lind & Ponack

[57] ABSTRACT

A process for producing novel 1,4-benzothiazine derivatives (I),

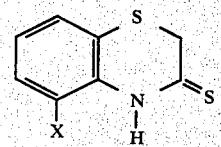

(in which X is a halogen atom) and their derivatives,

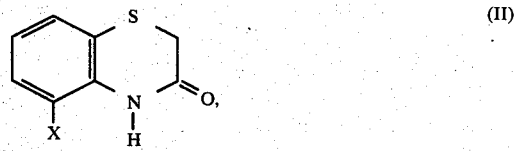

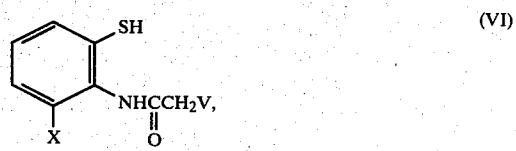

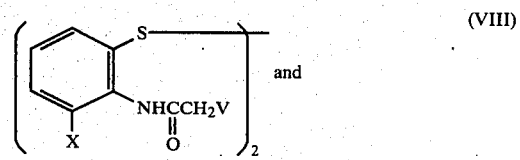

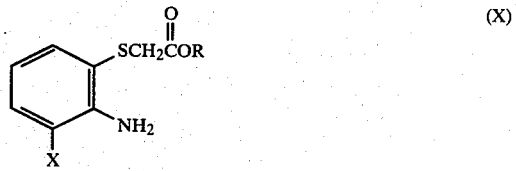

wherein R is a ($C_1$–$C_5$) alkyl, ($C_3$–$C_6$) cycloalkyl, phenyl, substituted phenyl, phenyl ($C_1$–$C_5$) alkyl or phenoxy ($C_1$–$C_5$) alkyl group; and herbicides containing these compounds as an active ingredient. Compound (I) is produced by the reaction between Compound (II) and phosphorus pentasulfide; Compound (II) is produced (1) by the reaction between an aminothiophenol (III),

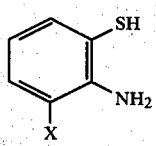

(in which X is a halogen atom), and a halogenated acetic acid, (2) by the ring closure of Compound (VI), (3) by the reduction and ring closure of Compound (VIII), and (4) by the hydrolysis and ring closure of Compound (X); Compound (VI) is produced by the reaction between Compound (III) and a halogenated acetyl halide; Compound (VIII) is produced by the oxidation of Compound (III) followed by reaction with a halogenated acetyl halide; and Compound (X) is produced by the reaction between Compound (III) and a halogenated acetic ester. Compounds (I), (II), (VI), (VIII) and (X) have a herbicidal activity.

4 Claims, No Drawings

HERBICIDAL DITHIO-BIS(HALOACETANILIDES)

This is a divisional application of application Ser. No. 28,801, filed Apr. 10, 1979, now U.S. Pat. No. 4,268,301.

The present invention relates to 1,4-benzothiazine derivatives of the formula (I),

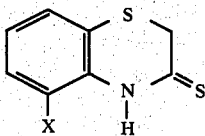
(I)

wherein X is a halogen atom, preferably Br or Cl, their production and herbicides characterized by containing them or their intermediates as an active ingredient.

According to the process of the present invention, the 1,4-benzothiazine derivatives (I) are obtained by reacting an 1,4-benzothiazine derivative of the formula (II),

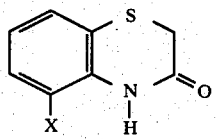
(II)

wherein X is as defined above, with phosphorus pentasulfide (referred to as "Process A" hereinafter). The 1,4-benzothiazine derivatives (II) are obtained by the following methods using aminothiophenol derivatives of the formula (III),

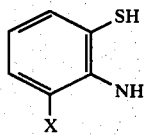
(III)

wherein X is as defined above, as a starting material.

(1) A method comprising reacting an aminothiophenol derivative (III) with a halogenated acetic acid of the formula (IV),

$$YCH_2COOH \qquad (IV)$$

wherein Y is a halogen atom, preferably chlorine or bromine, in the presence of a base (referred to as "Process B" hereinafter).

(2) A method comprising two steps:

In the first step, an aminothiophenol derivative (III) is reacted with a halogenated acetyl halide of the formula (V),

$$VCH_2CW \qquad (V)$$

wherein V and W are each a halogen atom, preferably chlorine or bromine, to obtain an aminothiophenol derivative of the formula (VI),

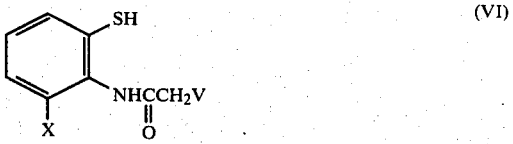
(VI)

wherein X and V are as defined above (referred to as "Process C-1" hereinafter).

In the second step, the resulting aminothiophenol derivative (VI) is converted to the objective 1,4-benzothiazine derivative (II) by ring closure reaction preferably in the presence of a base (referred to as "Process C-2" hereinafter). Hereinafter, the two steps, Processes C-1 and C-2, are combined into "Process C".

In this method (2), the objective compound (II) may also be obtained directly from the compounds (III) and (V) without isolating the compound (VI).

(3) A method comprising three steps:

In the first step, an aminothiophenol derivative (III) is oxidized into a bis-(2-amino-3-halophenyl) disulfide of the formula (VII),

(VII)

wherein X is as defined above (referred to as "Process D-1" hereinafter).

In the second step, the resulting disulfide (VII) is reacted with a halogenated acetyl halide (V) to obtain a bis-(3-halo-2-haloacetylaminophenyl) disulfide of the formula (VIII),

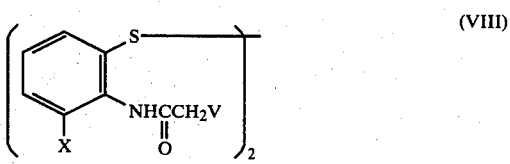
(VIII)

wherein V and X are as defined above (referred to as "Process D-2" hereinafter).

In the third step, the resulting disulfide (VIII) is converted to the objective 1,4-benzothiazine derivative (II) by reduction and ring closure reaction (referred to as "Process D-3" hereinafter).

Hereinafter, the three steps, Processes D-1, D-2 and D-3, are combined into "Process D".

(4) A method comprising two steps:

In the first step, an aminothiophenol derivative (III) is reacted with a halogenated acetic ester of the formula (IX),

$$QCH_2COR \qquad (IX)$$

wherein Q is a halogen atom (preferably chlorine or bromine) and R is a $(C_1-C_5)$ alkyl, $(C_3-C_6)$ cycloalkyl, phenyl substituted phenyl (preferably halogen atom, $(C_1-C_5)$ alkyl, $(C_1-C_5)$ alkoxy, nitro group, cyano group, amino group or phenoxy group), phenyl$(C_1-C_5)$ alkyl or phenoxy ($C_1$–$C_5$) alkyl group, to obtain an aminothiophenol derivative of the formula (X),

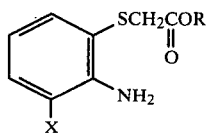 (X)

wherein X and R are as defined above (referred to as "Process E-1" hereinafter).

In the second step, the resulting compound (X) is converted to the objective 1,4-benzothiazine derivative (II) by hydrolysis and ring closure reaction (referred to as "Process E-2" hereinafter). The compounds (II) are novel when X is Br, I or F.

Hereinafter, the two steps, Processes E-1 and E-2, are combined into "Process E".

The 1,4-benzothiazine derivatives of the formula (I) are novel compounds, and the 1,4-benzothiazine derivatives of the formulae (I) and (II) have a strong herbicidal activity. Further, all the intermediate aminothiophenol derivatives (VI), (VIII) and (X), are novel compounds and they also have a herbicidal activity.

The present compounds of the formulae (I), (II), (VI), (VIII) and (X) have a strong herbicidal activity against grassy field weeds such as barnyard grass (*Echinochloa crus-galli*), large crabgrass (*Digitaria sanguinalis*), green foxtail (*Setaria viridis*) and water foxtail (*Alopecurus aequalis*); broad-leaved field weeds such as umbrella plant (*Cyperus difformis* L.), redroot pigweed (*Amaranthus retroflexus*), common lambsquarter (*Chenopodium album*), common purslane (*Portulaca oleracea*) and common chickweed (*Stellaria media*); and annual paddy field weeds such as barnyard grass (*Echinochloa crusgalli*), pickerel weed (*Monochoria vaginalis*), toothcup (*Rotala indica* Koehne) and *Dopatrium junceum*.

The compounds of the present invention are characterized in that they show a strong herbicidal activity against perennial paddy field weeds [e.g. perennial nutsedge (*Cyperus serotinus* Rottb), arrowhead sp. (*Sagittaria pygmaea* Miq), bulrush sp. (*Scirpus juncoides* var. Hotarui Ohwi), kuroguwai (*Eleocharis kuroguwai* Ohwi), slender spikerush (*Eleocharis acicularis*)], which have become a problem in recent years, as well as against the annual weeds by either pre-emergence treatment or foliage treatment, in other words, they show a broad herbicidal spectrum.

When the compounds of the present invention are used in fields, they are also very superior in the following points: They have a strong herbicidal activity against main weeds in fields; they show the activity by either soil treatment before the germination of weeds or foliage treatment at the beginning of growth; and besides they can be applied safely without doing damage to main crops (e.g. rice, soybean, cotton, corn, peanut, sunflower) as well as to vegetables (e.g. lettuce, radish).

Further, the compounds of the present invention are very useful as herbicides not only for paddy rice but also for various crops, vegetables, orchards, turfs, pasture lands, tea gardens, mulberry farms, rubber farms, forest lands and non-cultivation lands.

Also, the compounds of the present invention are low in toxicity to fishes and are high in safety to mammals.

Next, explanation will be given to a process for producing the present compounds.

In Process A, the present compounds (I) are obtained by reacting an 1,4-benzothiazine derivative (II) with phosphorus pentasulfide in a suitable organic solvent. The solvent includes for example benzene, toluene, xylene, chloroform, carbon tetrachloride, pyridine and mixtures thereof. Phosphorus pentasulfide is used within a range of 1/5 to 5 times by mole based on the compound (II). The reaction temperature varies within a range of 60° to 140° C. This reaction usually comes to an end in 0.1 to 10 hours. The present compounds (I) are isolated by filtering the reaction mixture while hot through Celite and removing the solvent by evaporation, or, when the solvent is pyridine, by pouring the reaction mixture into water preferably an aqueous acidic solution (e.g. dilute hydrochloric acid, dilute sulfuric acid). The compounds (I) thus obtained may further be purified by the common purification technique such as recrystallization or column chromatography.

In Process B, the objective compounds (II) are obtained by mixing an aminothiophenol derivative (III) and a halogenated acetic acid (IV) in a suitable solvent in the presence of a suitable base, and stirring the reaction mixture at a suitable temperature of 0° to 150° C. The amount of a halogenated acetic acid is preferably 1 to 1.5 times by mole based on the compound (III). The reaction is usually completed in 0.5 to 10 hours. When the compound (II) separates as crystals from the reaction system, it is filtered, washed with water and dried. In other cases, the reaction mixture is poured into water, and after made neutral if necessary, it is extracted with an organic solvent sparingly soluble in water. The organic layer is then washed with water, dried and freed from the solvent by evaporation to obtain the objective compound (II).

The solvent used in this reaction includes for example water, ethanol, methanol, benzene, toluene, xylene, tetrahydrofuran, dioxane, ethyl ether, chloroform, carbon tetrachloride, ethyl acetate, DMF, DMSO and mixtures thereof. The base used in this reaction includes for example tertiary amines (e.g. pyridine, triethylamine, trimethylamine), sodium hydroxide, potassium hydroxide, zinc hydroxide, magnesium hydroxide, sodium hydride, potassium tert-butoxide, sodium ethoxide and sodium methoxide. The compounds (II) thus obtained may further be purified by the common purification technique such as recrystallization or column chromatography.

The objective compounds (II) may be obtained by converting an aminothiophenol derivative (III), prior to reaction, to a salt using the foregoing base, and carrying out the above reaction in the absence of the base. The compounds (II) thus obtained may further be purified by the common purification technique such as recrystallization or column chromatography.

Process C:

In Process C-1, the objective compounds (VI) are obtained by reacting an aminothiophenol derivative (III) with a halogenated acetyl halide (V) in a suitable inert solvent in the presence of a base. The base includes for example tertiary amines (e.g. pyridine, triethylamine, trimethylamine), sodium hydroxide, potassium hydroxide, sodium hydride, potassium tert-butoxide, sodium ethoxide and sodium methoxide. The amounts of a halogenated acetyl halide (V) and the base are preferably 1 to 1.5 times by mole and 9/10 to 1 time by mole, respectively, based on the compound (III). The reaction temperature is within a range of 0° to 150° C. This reaction usually comes to an end in 0.1 to 10 hours. In the same manner as in Process B, the aminothiophenol derivative (III) may be converted to a salt, prior to reaction, using the foregoing base, and then allowed to react with a halogenated acetyl halide (V).

The objective compound (VI) is isolated as follows: The reaction mixture is freed from the solvent by evaporation, and the residue is extracted with addition of water and an organic solvent sparingly soluble in water, or the reaction mixture is poured into water and after made neutral if necessary, the aqueous solution is extracted with an organic solvent sparingly soluble in water; and in either case, the organic layer thus obtained is dried and freed from the solvent by evaporation to obtain the objective compound. The compounds (VI) thus obtained may further be purified by the common purification technique such as recrystallization or column chromatography.

In Process C-2, the objective compounds (II) are obtained by subjecting an aminothiophenol derivative (VI) to ring closure reaction in a suitable solvent in the presence of a base. The solvent includes for example water, ethanol, methanol, benzene, toluene, xylene, tetrahydrofuran, dioxane, ethyl ether, chloroform, carbon tetrachloride, ethyl acetate, DMF, DMSO and mixtures thereof. The base includes for example tertiary amines (e.g. pyridine, triethylamine, trimethylamine), sodium hydroxide, potassium hydroxide, sodium hydride, potassium tert-butoxide, sodium ethoxide and sodium methoxide. The reaction temperature varies within a range of 0° to 150° C. The amount of the base is preferably 1 to 5 times by mole based on the corresponding material.

The objective compound (II) is isolated as follows: The reaction mixture is freed from the solvent by evaporation, and the residue is extracted with addition of water and an organic solvent sparingly soluble in water, or the reaction mixture is poured into water and after made neutral if necessary, the aqueous solution is extracted with an organic solvent sparingly soluble in water; and in either case, the organic layer thus obtained is deried and freed from the solvent by evaporation to obtain the objective compound. When the objective compound separates as crystals from the reaction system, it is filtered, washed with water and dried. The compounds (II) thus obtained may further be purified by the common purification technique such as recrystallization or column chromatography.

Process D:

In Process D-1, the objective compounds (VII) are obtained by oxidizing an aminothiophenol derivative (III) with a suitable oxidizing agent in the presence or absence of a solvent. As the solvent, a basic water is particularly preferred, but other solvents such as ethanol, methanol, benzene, toluene, xylene, tetrahydrofuran, dioxane, ethyl ether, chloroform, carbon tetrachloride, ethyl acetate, DMF, DMSO and mixtures thereof are also utilized. The oxidizing agent includes for example oxygen, hydrogen peroxide and iodine. The molar ratio of the oxidizing agent to an aminothiophenol derivative (III) is in the range of 1 to 3. The reaction temperature is within a range of 0° to 140° C. This reaction usually comes to an end in 0.5 to 10 hours. The objective compound (VII) is isolated by extracting the reaction mixture with addition of water and an organic solvent sparingly soluble in water, and washing the organic layer with an aqueous dilute sodium hydrogen sulfite solution and then with water, followed by drying and removal of the solvent. When the objective compound separates as crystals from the reaction system, it is filtered, washed with water and dried. The compounds (VII) thus obtained may further be purified by the common purification technique such as recrystallization or column chromatography.

In Process D-2, the objective compounds (VIII) are obtained by reacting an aminothiophenol derivative (VII) with a halogenated acetyl halide (V) in a suitable solvent in the presence of a suitable base. The solvent includes for example water, ethanol, methanol, benzene, toluene, xylene, tetrahydrofuran, dioxane, ethyl ether, chloroform, carbon tetrachloride, ethyl acetate, DMF, DMSO and mixtures thereof. The base includes for example tertiary amines (e.g. pyridine, triethylamine, trimethylamine), sodium hydroxide, potassium hydroxide, sodium carbonate and potassium carbonate.

The amounts of a halogenated acetyl halide (V) and the base are preferably 2 to 2.5 times by mole based on the compound (VII). The reaction temperature is within a range of 0° to 150° C. This reaction usually comes to an end in 0.5 to 10 hours. The objective compound (VIII) is isolated by pouring the reaction mixture into water, extracting the aqueous solution with an organic solvent sparingly soluble in water, and washing the organic layer with water, followed by drying and removal of the solvent. The compounds (VIII) thus obtained may further be purified by the common purification technique such as recrystallization or column chromatography.

In Process D-3, the objective compounds (II) are obtained by reducing a bis-(3-halo-2-haloacetylaminophenyl) disulfide (VIII) with a suitable reducing agent in a suitable solvent followed by ring closure reaction (in the presence of a base. The solvent includes for example water, ethanol, methanol and mixtures thereof. As the reducing agent, sodium sulfide of 2 to 20 times by mole based on the disulfide (VIII) is preferred. As the base, sodium hydroxide, potassium hydroxide or aqueous ammonia of 2 to 10 times by mole based on the disulfide (VIII) is preferred.

The reaction temperature is within a range of 0° to 100° C., and the reaction usually comes to an end in 0.1 to 5 hours. The objective compound (II) is isolated as follows: The reaction mixture is poured into water and acidified with suitable mineral acid, and when the compound separates as crystals, it is filtered, washed with water and dried; and in other cases, the acidified solution is extracted with an organic solvent sparingly soluble in water, and the organic layer is washed with water and freed from the solvent by evaporation to obtain the objective compound. The compounds (II) thus obtained may further be purified by the common purification technique such as recrystallization or column chromatography.

Process E:

In Process E-1, the objective compounds (X) are obtained by reacting an aminothiophenol derivative (III) with a halogenated acetic ester (IX) in a suitable solvent in the presence of a suitable base. The molar ratio of compound (IX) to compound (III) is preferably 1 to 3, and that of base to compound (III) is preferably 1 to 1.5. The solvent includes for example water, ethanol, methanol, benzene, toluene, xylene, tetrahydrofuran, dioxane, ethyl ether, chloroform, carbon tetrachloride, ethyl acetate, DMF, DMSO and mixtures thereof. The base includes for example tertiary amines (e.g. pyridine, triethylamine, trimethylamine), sodium hydroxide, potassium hydroxide, sodium hydride, potassium tert-butoxide, sodium ethoxide and sodium methoxide. The reaction temperature is within a range of 0° to 140° C. The objective compound is isolated as follows: The reaction mixture is poured into water, and after made neutral if necessary, the aqueous solution is extracted with an organic solvent sparingly soluble in water, and then the organic layer is dried and freed from the solvent by evaporation to obtain the objective compound. The compounds (X) thus obtained may further be purified by the common purification technique such as recrystallization or column chromatography. In the same manner as in Process B, the aminothiophenol derivative (III) may be converted to a salt, prior to reaction, using the foregoing base, and then allowed to react with a halogenated acetic ester to obtain the objective compound (X).

In Process E-2, the objective compounds (II) are obtained by hydrolyzing an aminothiophenol derivative (X) in a suitable aqueous solvent in the presence of an acid, followed by ring closure reaction, or by hydrolyzing the derivative (X) in a suitable solvent in the presence of a base, followed by ring closure reaction under a neutral or acidic condition. As the solvent, water, methanol, ethanol and mixtures thereof are particularly preferred. As the base, sodium hydroxide and potassium hydroxide are preferred. The amount of the base is more than 1.0 time by mole, preferably 3 to 10 times by mole based on the compound (X). As the acid, common inorganic or organic acids are used, but mineral acids such as hydrochloric acid and sulfuric acid, and organic strong acids such as p-toluenesulfonic acid are preferred. The trace catalytic amount of the acid of more than 0.05 time by mole is enough for the reaction. The reaction temperature is within a range of 0° to 150° C. The reaction is usually completed in 0.5 to 10 hours. The objective compound is isolated as follows: The reaction mixture is acidified to a pH of less than 6, particularly preferably 1 to 3, and when the objective compound separates as crystals, it is filtered, washed with water and dried; and in other cases, water is added to the acidified solution as required, the aqueous solution is extracted with an organic solvent sparingly soluble in water, and the organic layer is washed with water, dried and freed from the solvent to obtain the objective compound. The compounds (II) thus obtained may further be purified by the common purification technique such as recrystallization or column chromatography.

The aminothiophenol derivatives of the formula (III) used as a starting material in the foregoing processes are obtained by the common synthetic method in the following literature: Heterocyclic compounds Vol. 5, pp 509 (edited by Robert C. Elderfield, New York, John Willy & Sons, Inc.).

Next, typical examples of the present compounds obtained by the foregoing processes will be shown, but these examples are not to be interpreted as limiting the invention thereto.

| Compound number | Chemical structure | Physical constant |
| --- | --- | --- |
| (1) | [structure with Cl, S, N-H, =O] | mp. 160–161° C. |
| (2) | [structure with Br, S, N-H, =O] | mp. 146–147° C. |
| (3) | [structure with F, S, N-H, =O] | mp. 190–191° C. |
| (4) | [structure with Cl, S, N-H, =S] | mp. 138–140° C. |
| (5) | [structure with Br, S, N-H, =S] | mp. 144–145° C. |
| (6) | [structure with F, S, N-H, =S] | mp. 131° C. |
| (7) | [structure with Cl, S-, NH-CO-CH$_2$-Cl]$_2$ | mp. 188–189° C. |
| (8) | [structure with Cl, S-, NH-CO-CH$_2$-Br]$_2$ | mp. 199–200° C. |
| (9) | [structure with Br, S-, NH-CO-CH$_2$-Cl]$_2$ | mp. 183–184° C. |
| (10) | [structure with Br, S-, NH-CO-CH$_2$-Br]$_2$ | mp. 190–191° C. |
| (11) | [structure with Cl, SH, NH-CO-CH$_2$-Cl] | mp. 186–187° C. |
| (12) | [structure with Cl, SCH$_2$COCH$_3$, NH$_2$] | $n_D^{27.5}$ 1.5872 |
| (13) | [structure with Cl, SCH$_2$COCH$_2$CH$_3$, NH$_2$] | $n_D^{26.5}$ 1.5733 |

| Compound number | Chemical structure | Physical constant |
|---|---|---|
| (14) | 2-NH$_2$-3-Cl-C$_6$H$_3$-SCH$_2$COCH(CH$_3$)$_2$ | $n_D^{26.5}$ 1.5598 |
| (15) | 2-NH$_2$-3-Cl-C$_6$H$_3$-SCH$_2$CO-cyclohexyl | $n_D^{26.5}$ 1.5717 |
| (16) | 2-NH$_2$-3-Cl-C$_6$H$_3$-SCH$_2$CO-C$_6$H$_5$ | $n_D^{26.5}$ 1.6125 |
| (17) | 2-NH$_2$-3-Cl-C$_6$H$_3$-SCH$_2$COCH$_2$-C$_6$H$_5$ | $n_D^{27.0}$ 1.6055 |
| (18) | 2-NH$_2$-3-Cl-C$_6$H$_3$-SCH$_2$CO(CH$_2$)$_2$O-(2,4-Cl$_2$-C$_6$H$_3$) | $n_D^{27.5}$ 1.6032 |
| (19) | 2-NH$_2$-3-Br-C$_6$H$_3$-SCH$_2$COCH$_2$ | $n_D^{25.0}$ 1.5912 |
| (20) | 2-NH$_2$-3-Br-C$_6$H$_3$-SCH$_2$CO-C$_6$H$_5$ | $n_D^{26.5}$ 1.6342 |

In the practical application of the present compounds, they may be applied as such or in any preparation form such as granules, wettable powders, emulsifiable concentrates or flowable formulations.

In producing such preparation forms, a solid or liquid carrier may be used. As the solid carrier, there may be given mineral powders (e.g. kaolin, bentonite, clay, montmorillonite, talc, diatomaceous earth, synthetic hydrated silicate, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, waxes and the like.

As the liquid carrier, there may be given alcohols (e.g. methyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methyl ethyl ketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion and spreading may be any of the nonionic, anionic, cationic and amphoteric type agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene polymers, oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts, oxyalkylamines and the like. But, the surface active agent is not of course limited to these compounds. And, if necessary, gelatin, casein, sodium alginate, starch, agar, or water-soluble high polymers (e.g. carboxymethyl cellulose, methyl cellulose, polyvinyl pyrrolidone, polyvinyl alcohol) may be used.

The foregoing preparations generally contain 1 to 95% by weight, preferably 5 to 80% by weight of active ingredient (including other ingredients mixed). A suitable amount of active ingredient applied is generally 1 to 200 g per are, preferably 3 to 50 g per are. Since, however, the amount depends upon the preparation forms, application times, application techniques, application sites and kinds of weed and crop, it may be properly increased or decreased irrespective of the aforesaid ranges.

The preparation examples of the present herbicides will be shown hereinafter.

PREPARATION EXAMPLE 1

Twenty-five parts by weight of the present compound (1), 2.5 parts by weight of dodecylbenzenesulfonate, 2.5 parts by weight of lignosulfonate and 70 parts by weight of diatomaceous earth are well mixed while being powdered. Thus, a wettable powder is obtained.

PREPARATION EXAMPLE 2

Thirty parts by weight of the present compound (7), 10 parts by weight of Sorpol SM 100 (an emulsifier, a registered trade mark of Tōhō Kagaku Co.) and 60 parts by weight of xylene are well mixed to obtain an emulsifiable concentrate.

PREPARATION EXAMPLE 3

Five parts by weight of the present compound (2), 1 part by weight of white carbon, 5 parts by weight of lignosulfonate and 89 parts by weight of clay are well mixed while being powdered. The mixture is then well kneaded with water, granulated and dried to obtain a granule.

PREPARATION EXAMPLE 4

Three parts by weight of the present compound (11), 1 part by weight of isopropyl phosphate, 66 parts by weight of clay and 30 parts by weight of talc are well mixed while being powdered to obtain a dust.

PREPARATION EXAMPLE 5

Fourty parts by weight of bentonite, 5 parts by lignosulfonate and 55 parts by weight of clay are well mixed while being powdered. The mixture is then well kneaded with water, granulated and dried to obtain a granule containing no active ingredient. Ninety-five parts by weight of the granule is then impregnated with 5 parts by weight of the present compound (14) to obtain a granule.

PREPARATION EXAMPLE 6

Ninety-five parts by weight of bentonite sieved to 16 to 48-mesh size is inpregnated with 5 parts by weight of the present compound (1) to obtain a granule.

PREPARATION EXAMPLE 7

Twenty-five parts by weight of the present compound (1), 2 parts by weight of polyvinyl alcohol (Gosenol KH-20 ®, a trade name of Nippon Gosei Co.; saponification degree 78.5–81.5%; polymerization degree 2000), 15 parts by weight of ethylene glycol, 3 parts by weight of sorbitan trioleate and 55 parts by weight of water are mixed and powdered under a wet condition until the size of dispersed particles becomes less than 3μ. Thus, a flowable formulation is obtained.

The compounds of the present invention may be used together with other herbicides to improve the activity as herbicides, and in some cases, a synergistic effect can be expected. As the other herbicides, there may be given phenoxy series herbicides such as 2,4-dichlorophenoxyacetic acid and 2-methyl-4-chlorophenoxyacetic acid (including esters and salts thereof); diphenyl ether series herbicides such as 2,4-dichlorophenyl-4'-nitrophenyl ether, 2,4,6-trichlorophenyl-4'-nitrophenyl ether, 2-chloro-4-trifluoromethylphenyl-3'-ethoxy-4'-nitrophenyl ether, 2,4-dichlorophenyl-4'-nitro-3'-methoxyphenyl ether and 2,4-dichlorophenyl-3'-methoxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine and 2-methylthio-4,6-bisisopropylamino-1,3,5-triazine; urea series herbicides such as 3-(3,4-dichlorophenyl)-1,1-dimethylurea, 3-(3,4-dichlorophenyl)-1-methoxy-1-methylurea and 1-(2,2-dimethylbenzyl)-3-p-tolylurea; carbamate series herbicides such as isopropyl N-(3-chlorophenyl)carbamate and methyl N-(3,4-dichlorophenyl)carbamate; thiocarbamate series herbicides such as S-(4-chlorobenzyl)-N,N-diethylthiolcarbamate and S-ethyl N,N-hexamethylenethiolcarbamate; acid anilide series herbicides such as 3,4-dichloropropionanilide, N-methoxymethyl-2,6-diethyl-α-chloroacetanilide, 2-chloro-2',6'-diethyl-N-(butoxymethyl)acetanilide and N-chloroacetyl-N-(2,6-diethylphenyl)glycine ethyl ester; uracil series herbicides such as 5-bromo-3-sec-butyl-6-methyluracil and 3-cyclohexyl-5,6-trimethyleneuracil; pyridinium chloride series herbicides such as 1,1'-dimethyl-4,4'-bispyridinium chloride; phosphorus series herbicides such as N,N-bis(phosphonomethyl)glycine, O-ethyl O-(2-nitro-5-methylphenyl)-N-sec-butylphosphoroamidothioate and S-(2-methyl-1-piperidylcarbonylmethyl) O,O-di-n-propyldithiophosphate; toluidine series herbicides such as α,α,α-trifluoro-2,6-dinitro-N,N-dipropyl-p-toluidine; 5-tert-butyl-3-(2,4-dichloro-5-isopropoxyphenyl)-1,3,4-oxadiazolin-2-one; 3-isopropyl-1H-2,1,3-benzothiadiazine-(4)-3H-one-2,2-dioxide; α-(β-naphthoxy)propionanilide; 4-(2,4-dichlorobenzoyl)-1,3-dimethylpyrazol-5-yl p-toluene sulfonate and the like. But, the herbicides are not of course limited to these examples.

The compounds of the present invention may be applied together with insecticides, nematocides, fungicides, plant growth regulators or fertilizers if necessary.

The present invention will be illustrated in more detail with reference to the following examples. The compounds are shown by the numbers described hereinbefore.

EXAMPLE 1 (PROCESS A)

5-Chloro-2,3-dihydro-1,4-benzothiazine-3-one (2.0 g) and phosphorus pentasulfide (2.0 g) were added to pyridine (5 ml), followed by stirring at 120° C. for 20 minutes. The reaction mixture was then poured into a dilute hydrochloric acid (50 ml), and the precipitated crystals were filtered, washed with water, dried and recrystallized from ethanol to obtain 1.9 g of the objective 5-chloro-2,3-dihydro-1,4-benzothiazine-3-thione (m.p. 138°–140° C.).

Elementary analysis:

|  | C(%) | H(%) | N(%) | Cl(%) |
|---|---|---|---|---|
| Calculated (as $C_8H_6NS_2Cl$) | 44.54 | 2.81 | 6.49 | 16.43 |
| Found | 44.51 | 2.77 | 6.32 | 16.58 |

EXAMPLE 2 (PROCESS B)

2-Amino-3-chlorothiophenol (2.5 g) was dissolved in a solution of sodium hydroxide (690 mg) in water (40 ml), and bromoacetic acid (2.4 g) was added thereto with stirring. After stirring at 70° C. for 3 hours, the precipitated crystals were filtered, washed with water and dried to obtain 2.98 g of the objective 5-chloro-2,3-dihydro-1,4-benzothiazine-3-one (m.p. 160°–161° C.).

Elementary analysis:

|  | C(%) | H(%) | N(%) | S(%) | Cl(%) |
|---|---|---|---|---|---|
| Calculated (as $C_8H_6NSOCl$) | 48.12 | 3.04 | 7.02 | 16.06 | 17.76 |
| Found | 48.15 | 3.13 | 6.97 | 16.09 | 17.82 |

EXAMPLE 3 (PROCESS B)

The zine salt (2.0 g) of 2-amino-3-chlorothiophenol was suspended in water (30 ml), and bromoacetic acid (1.6 g) was added thereto, followed by stirring at 70° C. for 3 hours. The precipitated crystals were filtered, washed with water and dried to obtain 1.8 g of the objective 5-chloro-2,3-dihydro-1,4-benzothiazine-3-one (m.p. 160°–161° C.).

Elementary analysis:

|  | C(%) | H(%) | N(%) | S(%) | Cl(%) |
|---|---|---|---|---|---|
| Calculated (as $C_8H_6NSOCl$) | 48.12 | 3.04 | 7.02 | 16.06 | 17.75 |
| Found | 48.33 | 3.21 | 7.10 | 16.14 | 17.63 |

EXAMPLE 4 (PROCESS C-1)

2-Amino-3-chlorothiophenol (1.6 g) and pyridine (0.8 g) were dissolved in benzene (20 ml), and chloroacetyl chloride (1.2 g) was gradually added dropwise thereto at room temperature (25° C.) with stirring. After the addition was finished, the reaction mixture was stirred at room temperature for 30 minutes, and the solvent was removed under reduced pressure. The residue obtained was washed with water, dried and recrystallized from chloroform to obtain 2.0 g of 3-chloro-2-chloroacetylaminothiophenol (m.p. 186°–187° C.).

| Elementary analysis: | | | | | |
|---|---|---|---|---|---|
| | C(%) | H(%) | N(%) | S(%) | Cl(%) |
| Calculated (as $C_8H_7NSOCl_2$) | 40.69 | 2.99 | 5.93 | 13.58 | 30.03 |
| Found | 40.52 | 3.13 | 5.76 | 13.48 | 30.22 |

EXAMPLE 5 (PROCESS C-2)

2-Chloroacetylamino-3-fluorothiophenol (2.0 g) was added to 2 N aqueous sodium hydroxide solution (25 ml), followed by stirring at room temperature (25° C.) for 3 hours. The precipitated crystals were filtered, washed with water and dried to obtain 1.5 g of the objective 5-fluoro-2,3-dihydro-1,4-benzothiazine-3-one (m.p. 190°–191° C.).

| Elementary analysis: | | | | |
|---|---|---|---|---|
| | C(%) | H(%) | N(%) | S(%) |
| Calculated (as $C_8H_6NSOF$) | 52.44 | 3.31 | 7.64 | 17.50 |
| Found | 52.36 | 3.44 | 7.75 | 17.41 |

EXAMPLE 6 (PROCESS D-1)

2-Amino-3-chloroaminothiophenol (1.6 g) was dissolved in a 2 N aqueous sodium hydroxide solution (10 ml), and 30% aqueous hydrogen peroxide (1.1 ml) was added dropwise thereto at room temperature (25° C.) with stirring. After stirring for 5 hours, the precipitated crystals were filtered, washed with water and dried to obtain 1.5 g of the objective bis-(2-amino-3-chlorophenyl) disulfide (m.p. 87°–88° C.).

| Elementary analysis: | | | | | |
|---|---|---|---|---|---|
| | C(%) | H(%) | N(%) | S(%) | Cl(%) |
| Calculated (as $C_{12}H_{10}N_2S_2Cl_2$) | 45.43 | 3.18 | 8.83 | 20.21 | 22.35 |
| Found | 45.27 | 3.16 | 8.84 | 20.34 | 22.19 |

EXAMPLE 7 (PROCESS D-2)

Bis-(2-amino-3-chlorophenyl) disulfide (2.5 g) and triethylamine (2.0 g) were dissolved in chloroform (60 ml), and chloroacetyl chloride (1.8 g) was gradually added dropwise thereto at room temperature (25° C.) with stirring. After the addition was finished, the reaction solution was stirred at room temperature (25° C.) for 8 hours, and the solvent was removed under reduced pressure. The residue obtained was washed with water, dried and recrystallized from ethanol to obtain 3.4 g of bis-(3-chloro-2-chloroacetylaminophenyl) disulfide (m.p. 188°–189° C.).

| Elementary analysis: | | | | | |
|---|---|---|---|---|---|
| | C(%) | H(%) | N(%) | S(%) | Cl(%) |
| Calculated (as $C_{16}H_{12}N_2S_2O_2Cl_4$) | 40.87 | 2.58 | 5.96 | 13.64 | 30.16 |
| Found | 40.61 | 2.79 | 5.80 | 13.68 | 30.38 |

EXAMPLE 8 (PROCESS D-3)

Bis-(3-chloro-2-chloroacetylaminophenyl) disulfide (5 g) was dissolved in ethanol (150 ml), and 28% aqueous ammonia (10 ml) and then sodium sulfide ($Na_2S.9-H_2O$, 15 g) were added thereto, followed by stirring at room temperature for 2 hours. Thereafter, water (100 ml) was added to the reaction mixture which was then acidified with conc. hydrochloric acid. The precipitated crystals were filtered and washed with water to obtain 1.6 g of the objective 5-chloro-2,3-dihydro-1,4-benzothiazine-3-one (m.p. 160°–161° C.).

| Elementary analysis: | | | | | |
|---|---|---|---|---|---|
| | C(%) | H(%) | N(%) | S(%) | Cl(%) |
| Calculated (as $C_8H_6NSOCl$) | 48.12 | 3.04 | 7.02 | 16.06 | 17.75 |
| Found | 47.91 | 3.11 | 7.12 | 16.27 | 17.63 |

EXAMPLE 9 (PROCESS E-1)

2-Amino-3-chlorothiophenol (2.5 g) was dissolved in a solution of sodium hydroxide (690 mg) in methanol (40 ml), and methyl bromoacetate (2.4 g) was added thereto with stirring. After stirring at 80° C. for 1 hour, the reaction mixture was cooled to room temperature, poured into water (200 ml) and then extracted with chloroform (30 ml) three times. The combined chloroform layer was washed with water, dried over magnesium sulfate and freed from the solvent under reduced pressure to obtain 2.5 g of the objective methyl 2'-amino-3'-chlorophenylacetate ($n_D^{27.5}$ 1.5872).

| Elementary analysis: | | | | |
|---|---|---|---|---|
| | C(%) | H(%) | N(%) | Cl(%) |
| Calculated (as $C_9H_{10}NO_2SCl$) | 46.65 | 4.36 | 6.05 | 15.30 |
| Found | 46.62 | 4.51 | 5.84 | 15.56 |

EXAMPLE 10 (PROCESS E-2)

Ethyl 2'-amino-3'-chlorophenylthioacetate (2.0 g) was dissolved in ethanol (5 ml), and a 1.0 N aqueous sodium hydroxide solution (45 ml) was gradually added dropwise thereto, followed by stirring at room temperature (25° C.) for 8 hours. Thereafter, the reaction mixture was acidified to a pH of 2 with addition of conc. hydrochloric acid, followed by stirring for 1 hour. The precipitated crystals were filtered, washed with water and dried to obtain 1.5 g of the objective 5-chloro-2,3-dihydro-1,4-benzothiazine-3-one (m.p. 160°–161° C.).

| Elementary analysis: | | | | | |
|---|---|---|---|---|---|
| | C(%) | H(%) | N(%) | S(%) | Cl(%) |
| Calculated (as $C_8H_6NSOCl$) | 48.12 | 3.04 | 7.02 | 16.06 | 17.76 |
| Found | 48.33 | 2.88 | 6.83 | 16.15 | 17.93 |

EXAMPLE 11

Pre-emergence Application Test

The seeds of weeds, large crabgrass, redroot pigweed and common lambsquarter, and those of crops, soybean and sunflower, were separately sowed in flower pots (diameter 10 cm) and covered with soil. The emulsifiable concentrate, which was prepared from the predetermined amount of each test compound, was diluted with water and applied to the soil by means of a hand sprayer. Thereafter, the flower pots were placed in a greenhouse, and 20 days after the soil treatment, herbicidal activity and phytotoxicity to crops were examined. The results are shown in Table 1. The herbicidal activity was expressed in numerals ranging from 0 to 5 as shown below. The phytotoxicity to crops was also expressed on the same standard as in herbicidal activity.

|   | Percentage of inhibition (%) |
|---|---|
| 0 | 0–9 |
| 1 | 10–29 |
| 2 | 30–49 |
| 3 | 50–69 |
| 4 | 70–89 |
| 5 | 90–100 |

TABLE 1

| Compound No. | Dosage (weight of active ingredient, g/a) | Weeds Large crab grass | Redroot pigweed | Common lambsquarter | Crops Soybean | Sunflower |
|---|---|---|---|---|---|---|
| (1) | 40 | 5 | 5 | 5 | 0 | 0 |
|  | 20 | 5 | 5 | 5 | 0 | 0 |
| (2) | 40 | 5 | 5 | 5 | 0 | 0 |
|  | 20 | 5 | 5 | 5 | 0 | 0 |
| (3) | 80 | 5 | 5 | 5 | 0 | 0 |
|  | 40 | 5 | 4 | 5 | 0 | 0 |
| (4) | 40 | 5 | 5 | 5 | 0 | 0 |
|  | 20 | 5 | 5 | 5 | 0 | 0 |
| (5) | 40 | 5 | 5 | 5 | 0 | 0 |
|  | 20 | 5 | 5 | 5 | 0 | 0 |
| (6) | 80 | 5 | 4 | 5 | 0 | 0 |
|  | 40 | 5 | 4 | 5 | 0 | 0 |
| (7) | 40 | 5 | 5 | 5 | 0 | 0 |
|  | 20 | 4 | 5 | 5 | 0 | 0 |
| (8) | 40 | 5 | 5 | 5 | 0 | 0 |
|  | 20 | 4 | 5 | 5 | 0 | 0 |
| (9) | 40 | 5 | 5 | 5 | 0 | 0 |
|  | 20 | 5 | 5 | 5 | 0 | 0 |
| (10) | 40 | 5 | 5 | 5 | 0 | 0 |
|  | 20 | 4 | 5 | 5 | 0 | 0 |
| (11) | 40 | 5 | 5 | 5 | 0 | 0 |
|  | 20 | 5 | 5 | 5 | 0 | 0 |
| (12) | 80 | 5 | 5 | 5 | 0 | 0 |
|  | 40 | 4 | 5 | 5 | 0 | 0 |
| (13) | 40 | 5 | 5 | 5 | 0 | 0 |
|  | 20 | 5 | 5 | 5 | 0 | 0 |
| (14) | 40 | 5 | 5 | 5 | 0 | 0 |
|  | 20 | 5 | 5 | 5 | 0 | 0 |
| (15) | 80 | 5 | 5 | 5 | 0 | 0 |
|  | 40 | 4 | 5 | 5 | 0 | 0 |
| (16) | 40 | 5 | 5 | 5 | 0 | 0 |
|  | 20 | 4 | 5 | 5 | 0 | 0 |
| (17) | 80 | 5 | 5 | 5 | 0 | 0 |
|  | 40 | 3 | 4 | 5 | 0 | 0 |
| (18) | 80 | 5 | 5 | 5 | 0 | 0 |
|  | 40 | 5 | 5 | 5 | 0 | 0 |
| (19) | 80 | 5 | 5 | 5 | 0 | 0 |
|  | 40 | 4 | 5 | 5 | 0 | 0 |
| (20) | 40 | 5 | 5 | 5 | 0 | 0 |
|  | 20 | 4 | 5 | 5 | 0 | 0 |

EXAMPLE 12

Wagner's pots (diameter 14 cm) were each filled with 1.5 kg of paddy field soil and kept under flooded conditions. The seedlings of rice plant at the 3-leaf stage were transplanted thereto, and then the seeds of barnyard grass were sowed and the tubers of arrowhead sp. and perennial nutsedge were planted therein. Thereafter, the required amount of each test compound was applied to the soil under flooded conditions. Twenty-five days after the application, the degree of herbicidal activity and phytotoxicity were examined on the transplanted, sowed and planted plants as well as broad-leaved weeds [e.g. pickerel weed, false pimpernel (*Linderna pyxidaria*), toothcup] which emerged spontaneously. The results are shown in Table 2.

At the above application, the test compounds were each formulated into a wettable powder and applied at a rate of 15 cc/pot by means of a pipette. The herbicidal activity was expressed in numerals ranging from 0 to 5 as shown below.

|   | Percentage of inhibition (%) |
|---|---|
| 0 | 0–9 |
| 1 | 10–29 |
| 2 | 30–49 |
| 3 | 50–69 |
| 4 | 70–89 |
| 5 | 90–100 |

The phytotoxicity was evaluated as follows: The ratios of height, number of tiller and total weight (dry weight) in the treated plot to those in the untreated plot were calculated, and the worst value of these calculated values was expressed in numerals ranging from 0 to 5 as shown below.

|   | Ratio to untreated plot (%) |
|---|---|
| 0 | 100 |
| 1 | 90–99 |
| 2 | 80–89 |
| 3 | 60–79 |
| 4 | 40–59 |
| 5 | 0–39 |

TABLE 2

| Compound No. | Dosage (weight of active ingredient, g/a) | Herbicidal activity Barnyard grass | Broad-leaved weeds | Arrowhead sp. | Perennial nutsedge | Phytotoxicity Rice plant |
|---|---|---|---|---|---|---|
| (1) | 20 | 5 | 5 | 5 | 5 | 0 |
|  | 10 | 5 | 5 | 5 | 5 | 0 |
| (2) | 20 | 5 | 5 | 5 | 5 | 0 |
|  | 10 | 5 | 5 | 5 | 5 | 0 |
| (3) | 80 | 5 | 5 | 3 | 5 | 0 |
|  | 40 | 4 | 5 | 1 | 3 | 0 |
| (4) | 20 | 5 | 5 | 5 | 5 | 0 |
|  | 10 | 5 | 5 | 5 | 5 | 0 |
| (5) | 20 | 5 | 5 | 5 | 5 | 0 |
|  | 10 | 5 | 5 | 5 | 5 | 0 |
| (6) | 80 | 5 | 5 | 3 | 4 | 0 |
|  | 40 | 3 | 5 | 0 | 3 | 0 |
| (7) | 40 | 5 | 5 | 5 | 5 | 0 |
|  | 20 | 5 | 5 | 5 | 5 | 0 |
| (8) | 40 | 5 | 5 | 5 | 5 | 0 |
|  | 20 | 5 | 5 | 5 | 5 | 0 |
| (9) | 40 | 5 | 5 | 5 | 5 | 0 |
|  | 20 | 5 | 5 | 4 | 3 | 0 |
| (10) | 40 | 5 | 5 | 5 | 5 | 0 |
|  | 20 | 5 | 5 | 5 | 5 | 0 |
| (11) | 40 | 5 | 5 | 5 | 5 | 0 |
|  | 20 | 5 | 5 | 5 | 5 | 0 |
| (12) | 40 | 5 | 5 | 5 | 5 | 0 |
|  | 20 | 5 | 5 | 5 | 5 | 0 |
| (13) | 40 | 5 | 5 | 5 | 5 | 0 |
|  | 20 | 5 | 5 | 5 | 5 | 0 |
| (14) | 40 | 5 | 5 | 5 | 5 | 0 |
|  | 20 | 3 | 5 | 4 | 3 | 0 |
| (15) | 40 | 5 | 5 | 5 | 5 | 0 |
|  | 20 | 4 | 5 | 3 | 4 | 0 |
| (16) | 40 | 5 | 5 | 5 | 5 | 0 |
|  | 20 | 5 | 5 | 5 | 5 | 0 |
| (17) | 20 | 5 | 5 | 5 | 5 | 0 |
|  | 10 | 5 | 5 | 5 | 5 | 0 |
| (18) | 40 | 5 | 5 | 5 | 5 | 0 |
|  | 20 | 5 | 5 | 5 | 5 | 0 |

TABLE 2-continued

| Compound No. | Dosage (weight of active ingredient, g/a) | Herbicidal activity | | | | Phytotoxicity Rice plant |
|---|---|---|---|---|---|---|
| | | Barnyard grass | Broadleaved weeds | Arrowhead sp. | Perennial nutsedge | |
| (19) | 40 | 5 | 5 | 5 | 5 | 0 |
| | 20 | 5 | 5 | 5 | 5 | 0 |
| (20) | 40 | 5 | 5 | 5 | 5 | 0 |
| | 20 | 5 | 5 | 5 | 5 | 0 |

EXAMPLE 13

Plastic trays [35 cm×25 cm×10 cm (high)] were filled with field soil, and the seeds of redroot pigweed, common lambsquarter, large crabgrass and barnyard grass were separately sowed in the trays and grown for 14 days in a greenhouse. The required amount of the test compound was sprayed to the foliage of the test plants over the top by means of a small hand sprayer. At this foliar application, the height of each test plant was as follows: Redroot pigweed and common lambsquarter, 2-6 cm; and large crabgrass and barnyard grass, 4-10 cm.

After the foliar application, the test plants were placed in the greenhouse for further 20 days, and herbicidal activity was examined on each test plant as follows: The aerial parts of the dead test plants were cut off and weighed (fresh weight); a ratio of the fresh weight in the treated plot to that in the untreated plot was calculated and expressed in percent; and the herbicidal activity was expressed on the criteria as shown below. At the foregoing foliar application, the required amount of each test compound was formulated into a wettable powder, dispersed in water of 3 liter/are and applied with addition of a wetting agent.

| Criteria for evaluation of herbicidal activity | | | | | | |
|---|---|---|---|---|---|---|
| | Rating value | | | | | |
| | 0 | 1 | 2 | 3 | 4 | 5 |
| Survival rate (%) | 90-100 | 70-89 | 50-69 | 30-49 | 10-29 | 0-9 |

TABLE 3

| Compound No. | Dosage (weight of active ingredient, g/a) | Evaluation of herbicidal activity | | | |
|---|---|---|---|---|---|
| | | Redroot pigweed | Common lambsquarter | Large crabgrass | Barnyard grass |
| (1) | 40 | 5 | 5 | 5 | 5 |
| | 20 | 5 | 5 | 5 | 5 |
| (2) | 40 | 5 | 5 | 5 | 5 |
| | 20 | 5 | 5 | 5 | 5 |
| (7) | 40 | 5 | 5 | 5 | 5 |
| | 20 | 5 | 5 | 5 | 4 |
| (11) | 40 | 5 | 5 | 5 | 5 |
| | 20 | 5 | 5 | 5 | 5 |

What we claim is:

1. A compound of the formula (VIII):

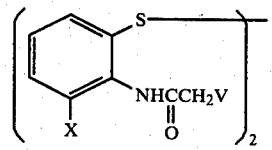

wherein each of X and V is a halogen atom.

2. The compound according to claim 1, wherein X and V are each a chlorine atom.

3. The compound according to claim 1, wherein X is a chlorine atom and V is a bromine atom.

4. The compound according to claim 1, wherein X is a bromine atom and V is a chlorine atom.

* * * * *